May 2, 1933. J. WHEELER ET AL Plant Pat. 64

CHRYSANTHEMUM

Filed Nov. 2, 1931 2 Sheets-Sheet 1

Inventors.
James Wheeler
Francis L. Wheeler
by Curtis Wyz Smith
Nathan Heard
Attys.

CHRYSANTHEMUM

Filed Nov. 2, 1931 2 Sheets-Sheet 2

Inventors.
James Wheeler
Francis L. Wheeler
by Curtis Nye Smith
Nathan Heard
Attys.

Patented May 2, 1933

Plant Pat. 64

UNITED STATES PATENT OFFICE

JAMES WHEELER AND FRANCIS L. WHEELER, OF NATICK, MASSACHUSETTS; FRANCIS LIONEL WHEELER EXECUTOR OF SAID JAMES WHEELER, DECEASED

CHRYSANTHEMUM

Application filed November 2, 1931. Serial No. 572,690.

This invention or discovery resides in the production of a new and distinct variety of the plant chrysanthemum which has been produced as the result of hybridization and subsequent asexual reproduction resulting in permanently fixed, novel and unique characteristics and habits.

The distinct and new variety of chrysanthemum of this invention is characterized among other things by, first, its peculiar style of bud and flower development, second, its abnormal or unique early flowering habit and, third, its extremely long period of continuous flowering.

The drawings illustrate a typical plant embodying the invention or discovery and a portion thereof illustrating the style of bud and flower development, the drawings being shown in black and white.

A unique characteristic or habit of this new chrysanthemum resides in its style of bud and flower development. The first buds appear and open into flowers on the terminals of the main stems, which are substantially stiff and erect. As the plant develops, the lateral branches are produced and on these lateral branches appear new buds opening into flowers. Then sub-lateral branches are produced and on these sub-lateral branches in turn appear new buds which open into flowers. So the growth, branching, budding, and flowering proceeds with the characteristic or habit that the budding and flowering first develops near the bottom of the plant and gradually proceeds upward first on the terminals, then on the lateral branches, then on the sub-lateral branches, and so on seriatim. While the order of budding and flowering is closely as indicated, some of the upper sub-laterals may, and often do, flower before some of the lower laterals or sub-laterals, but a unique characteristic of the plant is, as set forth, the continuous and successive development of the buds and flowers, first on the terminals, then on the laterals, then on the sub-laterals, and so on indefinitely. As the plant develops, the lateral branches grow rapidly, throwing the lateral and sub-lateral flowers well above the first terminal flowers, thus giving a continuous succession of flowers. As the earlier flowers mature, they are superseded by buds appearing and producing sub-lateral flowers from the axils of many of the leaves.

The plant is compact when grown out-of-doors. The foliage is usually of a deep green shade and sufficiently abundant to serve as a foil for the flowers that cover the entire plant. The plants normally attain a height of about thirty inches, but under some circumstances, and especially when forced under glass, reach a greater height with increased length of stem.

A second unique characteristic or habit of this new chrysanthemum is that it begins to flower unusually early. In the latitude of Massachusetts under normal garden conditions the flowers begin to appear during the latter part of July, thus advancing the chrysanthemum season to a marked degree.

A third unique characteristic or habit of this new chrysanthemum resides in its extremely long period of flowering, rendering it, as compared with other chrysanthemums, an everflowering variety. From the time the first buds and flowers appear, there is a continuous succession of buds and flowers until the end of the season, or, in the latitude of Massachusetts, from the latter part of July on through August, September, and October, or until the advent of frost. Thus the new chrysanthemum is distinguished from all other chrysanthemums where the flowers develop substantially at one time and with no marked tendency towards a recurring flowering period.

Figure 1:
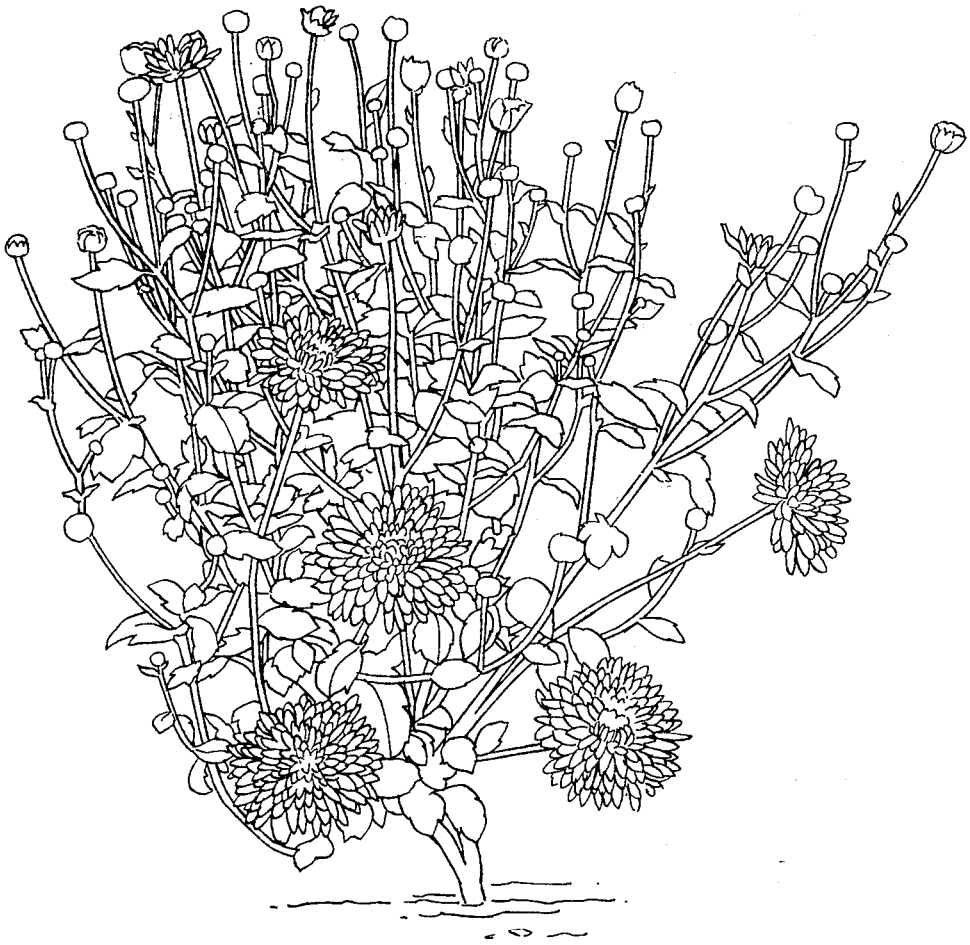
Fig. 1 is a close reproduction of one of the plants embodying this invention or discovery as it grows in the field.
Figure 2:
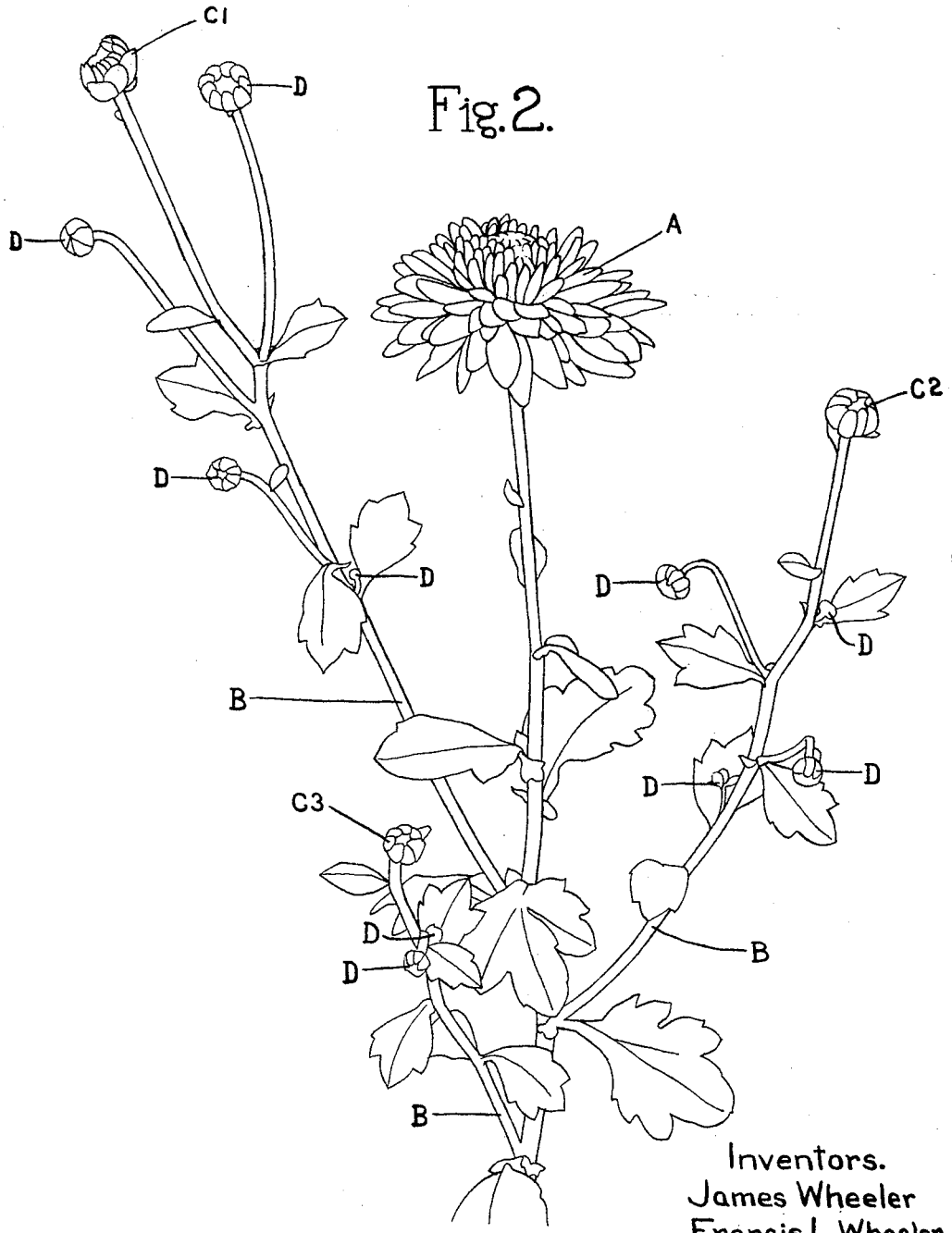
Fig. 2 is a detail of a portion of such a plant to show the style of bud and flower development.

Fig. 1 of the drawings shows a typical plant with the flowers blooming near the bottom or base of the plant and with the buds and flowers developing on the laterals, sub-laterals, and so on, up toward the top of the plant. In Fig. 2 of the drawings a terminal flower A is shown fully developed. Three lateral branches B are shown extending in different directions from the main stem carrying the terminal A and these are shown as bearing the lateral buds $C^1$, $C^2$, and $C^3$ next to develop into flowers. A number of sub-laterals are also shown branching from the laterals $C^1$, $C^2$, and $C^3$, and developing buds D which will open into flowers after the lateral buds. This figure indicates the general type of development of the bud and flower, although, as already pointed out, some of the upper sub-laterals may flower before some of the lower ones.

The characteristics and habits of the new chrysanthemum have been permanently fixed since its discovery as a result of hybridization by a long period of asexual reproduction until it is now recognized as an ideal combination of a hardy garden plant, a superb extra-early forcing variety and habits of extreme early flowering and continuous flowering over a long period of many weeks.

The flower is of the large-flowering Pompom type, specimen individual flowers being 3″ to 3½″ in diameter. There is no variation in habit or color other than the variation which commonly exists because of climatic or seasonal conditions during the blooming period.

When the first blooms appear, the color is apricot orange (Ridgway plate XIV), showing a deeper shade at the base of the petals and tinted on the outer edge of the petals to orange, capucine yellow, and orange buff (Ridgway plate III). As the season advances, all of the shades deepen and with the advent of cool nights and colder temperatures, the base color changes to cinnamon-rufous (Ridgway plate XIV), and the tints on the outer edge of the petals vary from orange rufous through orange chrome to salmon orange (Ridgway plate II).

It will be understood that allowance is to be given in the production of the chrysanthemum as the size of the bloom, the color shades, the vigor of the plant and other features thereof will vary somewhat on account of differences in soil, cultivation, environment and climate.

The new chrysanthemum is asexually reproduced, preferably by cuttings, and cannot be reproduced other than asexually.

Having thus described the invention, what is claimed as new, and desired to be secured by Letters Patent, is:

A chrysanthemum plant as shown and described characterized by its bud and flower development, in which characteristically the first or terminal growths develop the first buds and flowers, in which the laterals next develop buds and flowers, and in which the sub-laterals next develop buds and flowers, and so on seriatim from near the bottom of the plant upward, and by its early flowering and its continuous flowering thereafter throughout an abnormally long period exemplified as from late July throughout October in the latitude of Massachusetts.

In testimony whereof, we have signed our names to this specification.

JAMES WHEELER.
FRANCIS L. WHEELER.